US012605112B2

(12) United States Patent
Nalluri

(10) Patent No.: US 12,605,112 B2
(45) Date of Patent: Apr. 21, 2026

(54) DEVICE FOR DETECTING A BLOOD VESSEL

(71) Applicant: Bard Access Systems, Inc., Salt Lake City, UT (US)

(72) Inventor: Likhith Nalluri, Brea, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 79 days.

(21) Appl. No.: 18/216,046

(22) Filed: Jun. 29, 2023

(65) Prior Publication Data

US 2025/0000456 A1     Jan. 2, 2025

(51) Int. Cl.
*A61B 5/00*          (2006.01)

(52) U.S. Cl.
CPC ............ *A61B 5/489* (2013.01); *A61B 5/0075* (2013.01); *A61B 5/681* (2013.01); *A61B 5/7264* (2013.01)

(58) Field of Classification Search
CPC ...... A61B 5/489; A61B 5/0075; A61B 5/7264
See application file for complete search history.

(56) References Cited

U.S. PATENT DOCUMENTS

2017/0231553 A1 * 8/2017 Igarashi et al. .......... A61B 5/00
2021/0212616 A1   7/2021 Honore et al.

FOREIGN PATENT DOCUMENTS

| | | | |
|---|---|---|---|
| JP | 4964491 B2 | 6/2012 | |
| WO | 2006131881 A1 | 12/2006 | |
| WO | WO2010029521 A2 * | 9/2009 | ........... A61B 5/1455 |
| WO | WO 2020150489 A1 * | 7/2020 | .............. A61M 5/42 |

OTHER PUBLICATIONS

Leppänen et al. ("Pulse Oximetry: The Working Principle, Signal Formation, and Applications", Springer Nature, 2022, p. 205-218). (Year: 2022).*

PCT/US2024/036220 filed Jun. 28, 2024 International Search Report and Written Opinion dated Sep. 20, 2024.

* cited by examiner

*Primary Examiner* — Anne M Kozak
*Assistant Examiner* — Kaitlyn Eunji Kim
(74) *Attorney, Agent, or Firm* — Rutan & Tucker LLP

(57) ABSTRACT

A blood vessel detection device includes a pair of light sources that project lights having different wavelengths through the skin into a detection area of a patient and a photodetector that receives reflected lights originating from the light sources. Logic of a microcontroller of the device processes the intensity data related to the reflected lights having the different wavelengths to determine the presence of a blood vessel within the detection area and/or the identity of the blood vessel as a vein or an artery. The wavelengths are chosen such that hemoglobin within a blood vessel reduces the reflected light intensity different amounts according to an oxygen content of the hemoglobin. The intensities of one or both reflected lights is used to detect the presence of a blood vessel and a difference or a ratio of the intensities is used to identify the blood vessel as a vein vs an artery.

10 Claims, 4 Drawing Sheets

*FIG. 1A*
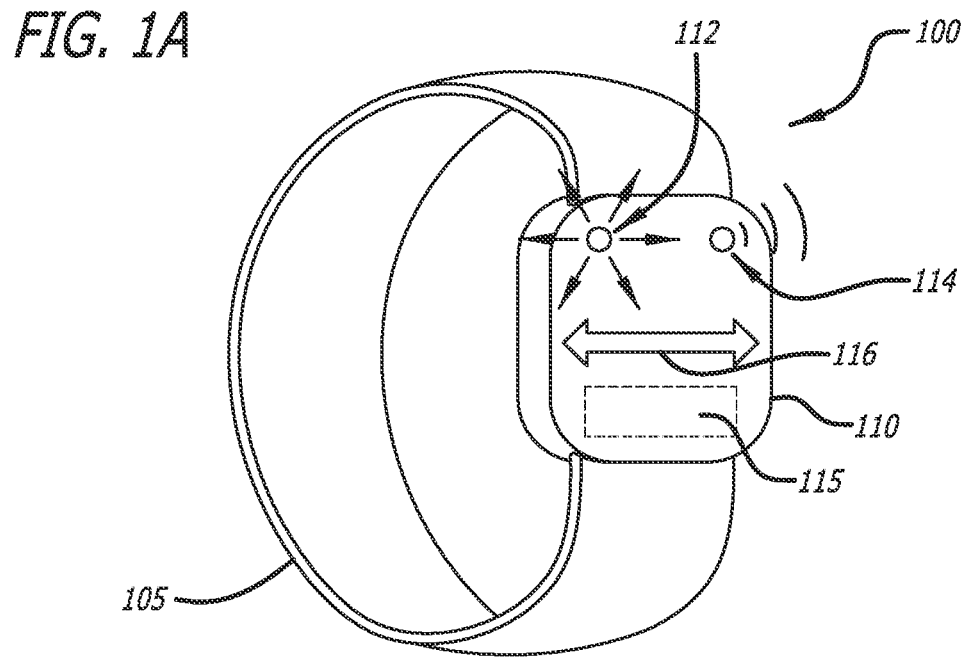
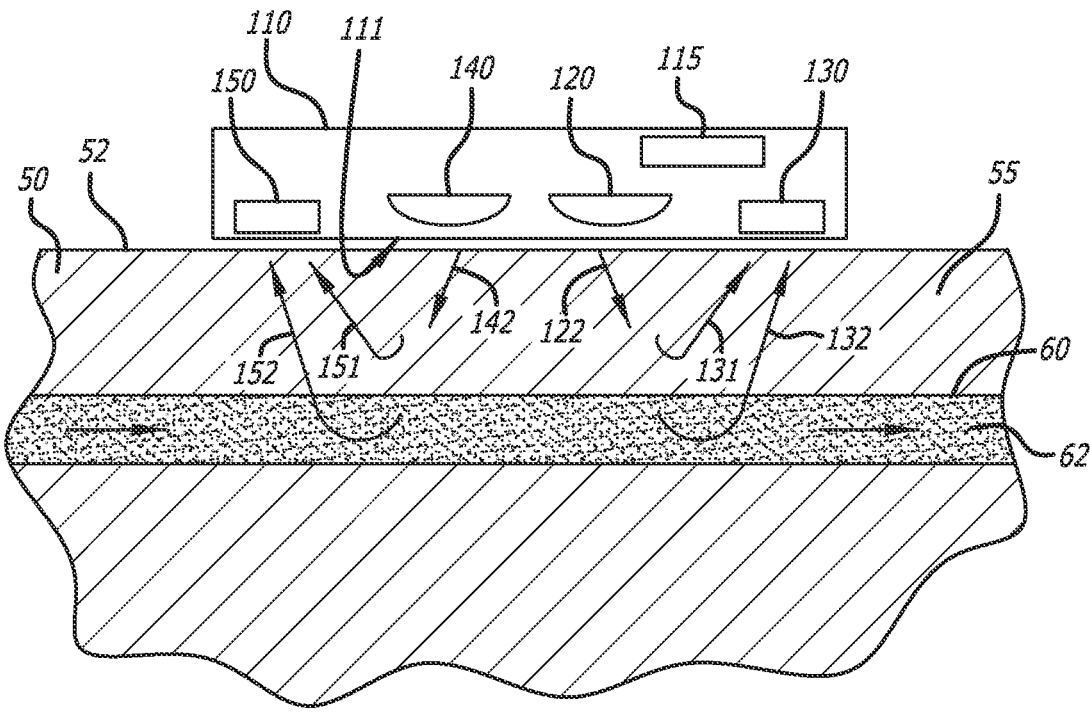
*FIG. 1B*

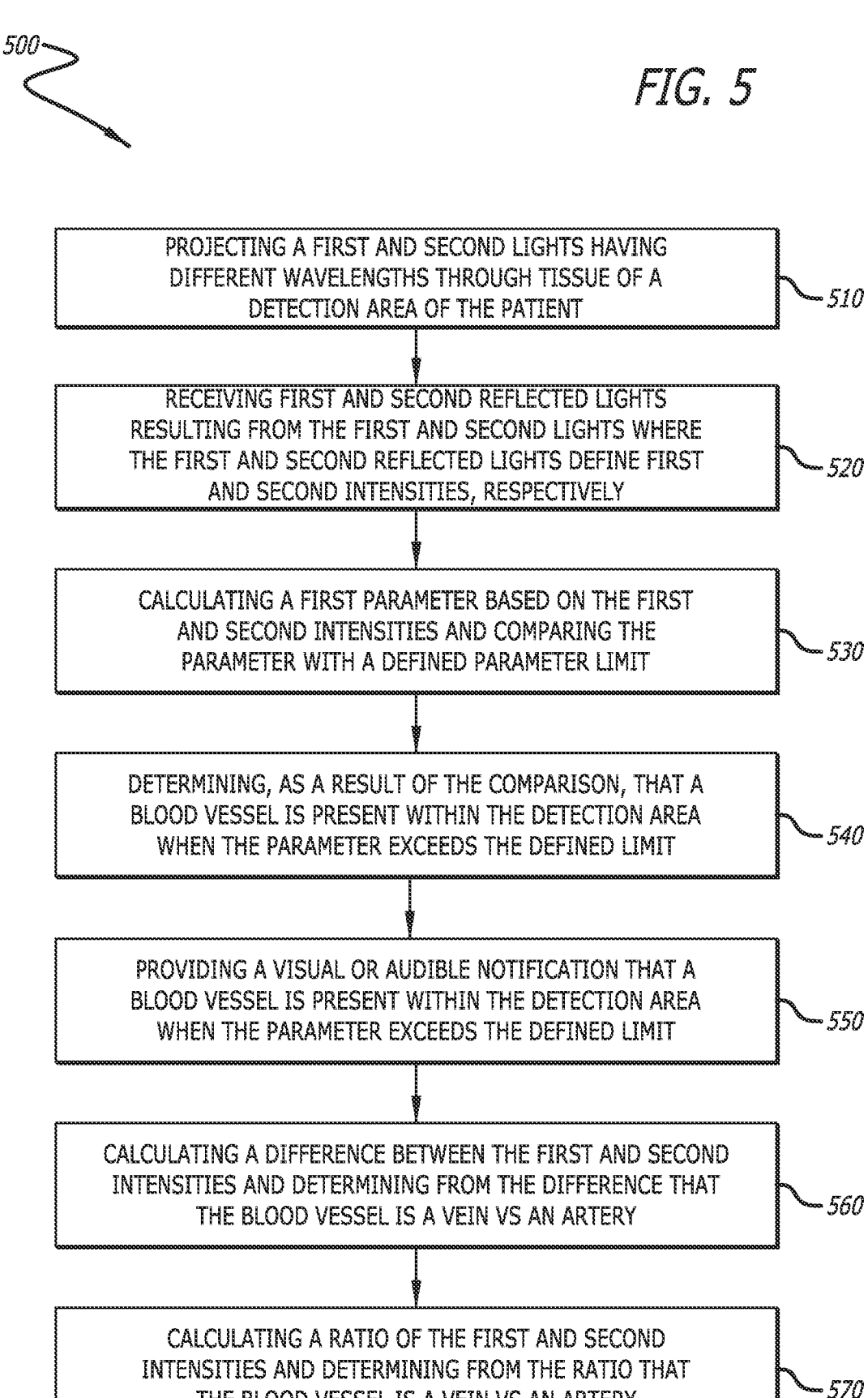

PROJECTING A FIRST AND SECOND LIGHTS HAVING DIFFERENT WAVELENGTHS THROUGH TISSUE OF A DETECTION AREA OF THE PATIENT — *510*

RECEIVING FIRST AND SECOND REFLECTED LIGHTS RESULTING FROM THE FIRST AND SECOND LIGHTS WHERE THE FIRST AND SECOND REFLECTED LIGHTS DEFINE FIRST AND SECOND INTENSITIES, RESPECTIVELY — *520*

CALCULATING A FIRST PARAMETER BASED ON THE FIRST AND SECOND INTENSITIES AND COMPARING THE PARAMETER WITH A DEFINED PARAMETER LIMIT — *530*

DETERMINING, AS A RESULT OF THE COMPARISON, THAT A BLOOD VESSEL IS PRESENT WITHIN THE DETECTION AREA WHEN THE PARAMETER EXCEEDS THE DEFINED LIMIT — *540*

PROVIDING A VISUAL OR AUDIBLE NOTIFICATION THAT A BLOOD VESSEL IS PRESENT WITHIN THE DETECTION AREA WHEN THE PARAMETER EXCEEDS THE DEFINED LIMIT — *550*

CALCULATING A DIFFERENCE BETWEEN THE FIRST AND SECOND INTENSITIES AND DETERMINING FROM THE DIFFERENCE THAT THE BLOOD VESSEL IS A VEIN VS AN ARTERY — *560*

CALCULATING A RATIO OF THE FIRST AND SECOND INTENSITIES AND DETERMINING FROM THE RATIO THAT THE BLOOD VESSEL IS A VEIN VS AN ARTERY — *570*

DEVICE FOR DETECTING A BLOOD VESSEL

BACKGROUND

Accessing a vein for IV therapy may generally include low risk for patient harm. However, the risk may increase for some patients when the location of a vein may be difficult to identify. Patient characteristics such as weight or skin color may add to the complexity the locating of a vein. Another common risk associated with vascular access is mistaking an artery for a vein. Some medical devices and systems utilize imaging technology to locate and identify blood vessels. However, such device can be relatively bulky and costly, and may require significant training for use. It has be shown that when devices are simple and less costly, they are more likely to be used. As such, there is a need for simple, small, less costly devices that clinicians may use to locate and identify blood vessels.

Disclosed herein are devices and methods that address the forgoing.

SUMMARY

Disclosed herein is a blood vessel detection device that, according to some embodiments, includes a device module configured for placement on a skin surface of a patient, where the device module includes (i) a first light source configured to project a first light having a first wavelength through a skin surface and into a detection area of a patient, where the detection area is located beneath the device module; (ii) a second light source configured to project a second light having a second wavelength through the skin surface and into the detection area, where the second wavelength is different from the first wavelength; (iii) a photodetector configured to receive a first reflected light resulting from the first light and a second reflected light resulting from the second light; and (iv) a console coupled with the first and second light sources and the photodetector. The console includes a microcontroller that having a processor and a memory, where logic stored in the memory, when executed by the processor, performs operations of the device. The operations include (i) receiving first light data originating from the photodetector including a first intensity of the first reflected light; (ii) receiving second light data originating from the photodetector including a second intensity of the second reflected light; (iii) calculating a first parameter of the first and second intensities; and (iv) determining from the first parameter the presence of a blood vessel within the detection area.

In some embodiments, the first wavelength is within the red spectrum, and the second wavelength is within the infrared spectrum in some embodiments, the first wavelength may be about 660 nm, and the second wavelength may be about 940 nm. The first light source, the second light source and the photodetector may arranged in a linear array. In some embodiments, the first parameter is a combination of the first and second intensities.

In some embodiments, determining the presence of a blood vessel includes comparing the combination of the first and second intensities with an intensity limit stored in the memory and determining that the blood vessel is present within the detection area when the combination of the first and second intensities is less than the intensity limit.

In some embodiments, the operations further include calculating a second parameter of the first and second intensities and determining from the second parameter that a blood vessel present within the detection area is a vein or is an artery. In some embodiments, the second parameter is a difference between the first intensity and the second intensity.

In some embodiments, the operations further include calculating a third parameter of the first and second intensities and determining from the third parameter that a blood vessel present within the detection area is a vein or is an artery.

In some embodiments, the third parameter is a ratio of the first and second intensities, the ratio defined by the first intensity divided by the second intensity.

In some embodiments, determining from the third parameter that a blood vessel present within the detection area is a vein or is an artery includes comparing the ratio with a ratio limit stored in the memory and determining that the blood vessel is a vein when the ratio is less than the ratio limit.

In some embodiments, operations include pulsing the first and second light sources at a rate between 30 and 40 pulses per second.

In some embodiments, the device further includes an attachment mechanism coupled with the device module, where the attachment mechanism is configured to secure device module to the patient. In some embodiments, the attachment mechanism includes a band or a strap configured to extend around an extremity of the patient.

In some embodiments, the device module further includes least one of a number of visual notification devices or a number of audio notification devices, and the operations further include providing at least one of a visual or audible notification when a blood vessel is present within the detection area. In some embodiments, the operations further include providing at least a second one of a visual or audible notification when a blood vessel present within the detection area is determined to be a vein.

Also disclosed herein is a method of detecting a blood vessel within a patient that, according to some embodiments, includes (i) projecting a first light having a first wavelength through tissue of a detection area of the patient; (ii) projecting a second light having a second wavelength through the tissue of the detection area, where the second wavelength is different from the first wavelength; (iii) receiving a first reflected light resulting from the first light, where the first reflected light defines a first intensity; (iv) receiving a second reflected light resulting from the second light, where the second reflected light defines a second intensity; (v) calculating a first parameter based on the first intensity and the second intensity; (vi) comparing the parameter with a defined parameter limit; (vii) determining, as a result of the comparison, that a blood vessel is present with the detection area when the parameter exceeds the defined limit; and (viii) providing a visual or audible notification that a blood vessel is present within the detection area when the parameter exceeds the defined limit.

In some embodiments of the method, the first wavelength is within the red spectrum, and the second wavelength is within the infrared spectrum.

In some embodiments, the first parameter is a combination of the first and second intensities.

In some embodiments, the method further includes (i) calculating a difference between the first and second intensities; (ii) comparing the difference with a defined difference limit; (iii) determining, as a result of the comparison, that a blood vessel is a vein vs an artery; and (iv) providing a visual or audible notification that a vein is present within the detection area when the difference exceeds a defined difference limit.

In some embodiments, the method further includes (i) calculating a ratio of the first and second intensities; (ii) comparing the ratio with a defined ratio limit; (iii) determining, as a result of the comparison, that a blood vessel is a vein; (iv) providing a visual or audible notification that a vein is present within the detection area when the ratio exceeds a defined ratio limit.

In some embodiments, calculating the ratio includes dividing the first intensity by the second intensity, and exceeding the defined ratio limit is defined by the ratio having a greater numerical value than the defined ratio limit.

These and other features of the concepts provided herein will become more apparent to those of skill in the art in view of the accompanying drawings and following description, which describe particular embodiments of such concepts in greater detail.

DRAWINGS

FIG. 1A illustrates a perspective view of a blood vessel detection device, according to some embodiments.

FIG. 1B is a side cross-sectional view of a device module of FIG. 1A in use with a portion of a patient, in accordance with some embodiments.

FIG. 5 illustrates a block diagram of a method for detecting and identifying a blood vessel within a patient, in accordance with some embodiments.

DESCRIPTION

Figure 2:
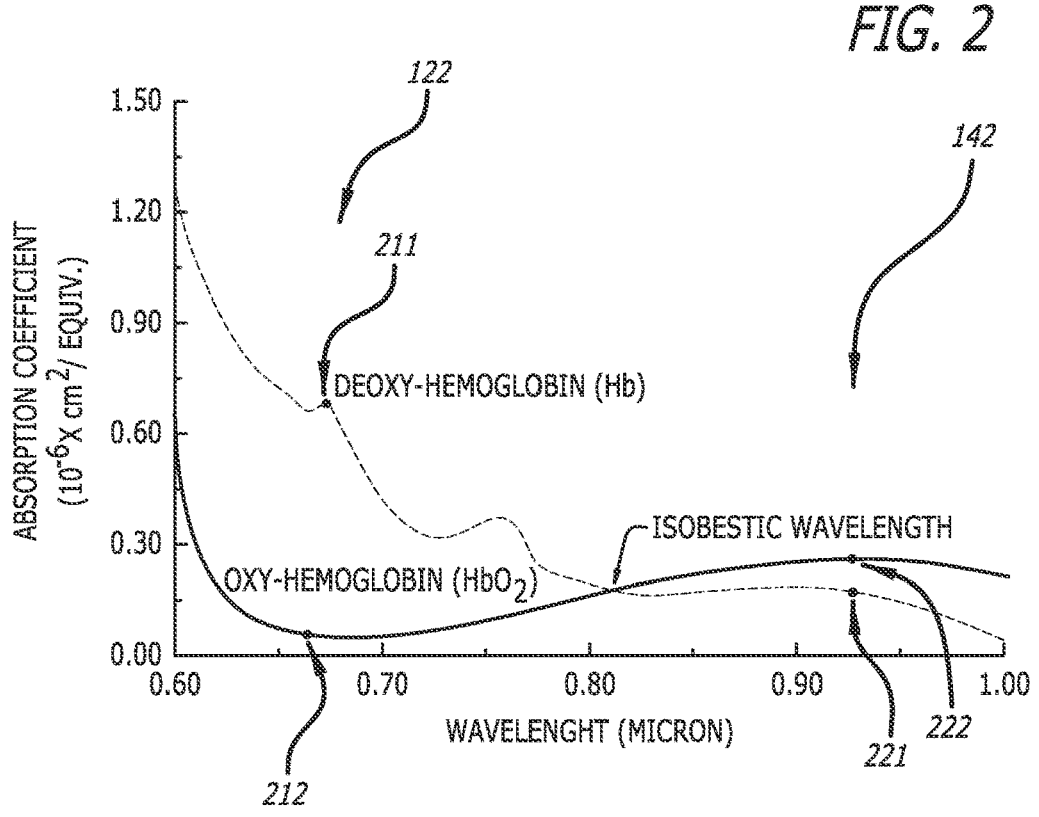
FIG. 2 illustrates an exemplary graph depicting absorption coefficients related to oxygen content of hemoglobin as a function of wavelength, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled with," and "in communication with" refer to any form of interaction between two or more entities, including but not limited to physical, mechanical, electrical, magnetic, electromagnetic, fluid, wireless, and thermal interaction. Two components may be coupled with each other even though they are not in direct contact or communication with each other. For example, two components may be coupled with each other through an intermediate component.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art. The phrase "exceeding a limit" as used herein is non-directional. In other words, a parameter may exceed a limit by dropping below a limit or by going above the limit.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method. Additionally, all embodiments disclosed herein are combinable and/or interchangeable unless stated otherwise or such combination or interchange would be contrary to the stated operability of either embodiment.

FIG. 1A illustrates a vein (or blood vessel) detection device (device) 100 according to one embodiment. The device 100 is generally configured for placement on a patient, such as on an arm for example. The device 100 may include an attachment mechanism 105, such as the flexible arm band shown in FIG. 1A. Other attachment mechanisms are also considered, such as a strap, a clamp, or an adhesive and as such are included in this disclosure. In some embodiments, the attachment mechanism 105 may be omitted, where according to some embodiments, a user (e.g., a clinician) may apply the device 100 to the patient and hold the device in contact with the patient.

The device 100 is generally configured to determine if a vein is located within the patient beneath a device module 110 of the device 100. In other words, the device 100 is configured to determine if the device module 110 is located over a vein of the patient. The device 100 is configured to provide a notification to the user when the device 100 detects a vein beneath the device module 110. The notification may include a visual or audible notification or both. According to the illustrated embodiment, the device 100 may include a number (e.g., 1, 2, 3, or more) illuminating devices 112 (e.g., an LED) that illuminate (or provide another visual indication, such as a color change, for example) when the device 100 detects a blood vessel beneath the device module 110 and/or identifies that a blood vessel is a vein vs an artery. Similarly, the device 100 may include a number (e.g., 1, 2, 3, or more) of audio devices 114 that provide or alter a sound when the device 100 detects a blood vessel beneath the device module 110 and/or identifies that a blood vessel is a vein vs an artery.

According to one embodiment, the device module 110 may include an indicium 116 (e.g., the arrow as illustrated) and detecting the vein beneath the device module 110 may include detecting the vein in alignment with (i.e., located directly beneath) the indicum 116. In use, the user may move or reposition the device module 110 across the patient (e.g., rotate about an arm) until the notification indicates that the device module 110 (or more specifically the indicum 116) is located over a vein. In such an instance, the user may be confident that a vein is disposed beneath the device module 110 in alignment with the indicium 116.

FIG. 1B is a side cross-sectional illustration of the device module 110 in use with a patient 50. The device module 110 is placed adjacent to (e.g., in contact with) a skin surface 52 of the patient 50. A blood vessel 60 having blood 62 passing therethrough is disposed beneath the device module 110. Tissue 55 is disposed between the device module 110 and the blood vessel 60. The device module 110 includes a first light source 120 and a second light source 140. The device module 110 further includes a number (e.g., 1, 2, 3 or more) photodetectors, such as a first photodetector 130, and a second photodetector 150. The device module 110 further includes a console 115 which generally governs the operation of the device module 110.

In the illustrated embodiment, the first light source 120, the second light source 140, the first photodetector 130, and the second photodetector 150 are linearly arranged along the bottom surface 111 of the device module 110. Further, the indicum 116 may be located directed opposite and in alignment with the first light source 120, the second light source 140, the first photodetector 130, and the second photodetector 150. The placement order of the first light source 120, a second light source 140, a first photodetector 130, and a second photodetector 150 as illustrated in FIG. 1B is only exemplary and thus not limiting. While the illustrated embodiment, includes two photodetectors 130, 150, other embodiments may include more or less than two photodetectors. For example, the operation of the two photodetectors 130, 150 may be combined into a single photodetector.

The first light source 120, which may include a light emitting diode (LED), is configured to project a first light 122 downward from the bottom surface 111 of the device module 110 so that the first light 122 impinges onto the skin surface 52 and travels through the tissue 55 to the blood vessel 60. The first light 122 includes a first wavelength within the red spectrum that is equal to about 660 nm. The second light source 140, which may also include a LED, is configured to project a second light 142 downward from the bottom surface 111 of the device module 110 so that the second light 142 (similar to the first light 122) impinges onto the skin surface 52 and travels through the tissue 55 to the blood vessel 60. The second light 122 includes a second wavelength within the infrared spectrum that is equal to about 940 nm.

The first light 122 and second light 142 reflect off the tissue 55 and the blood 62 and the photodetectors 130, 150 detect and receive the reflect light. A relatively large portion of a total reflected light is composed of light reflected off (scattered by) the tissue 55, as designated by the first scattered light 131 and the second scattered light 151. When the blood vessel 60 is present a portion of the total reflected light is absorbed (e.g., by pulsatile absorption) by the blood 62, such that the amount of reflected light received by the photodetectors 130, 150 is greater in the absence of the blood vessel 60 than when the blood vessel 60 is present. As such, a decrease in the reflected light as detected by the photodetectors 130, 150 may indicate the presence of the blood vessel 60 beneath the device module 110.

Portions of the first light 122 and the second light 142 reflect off the blood 62 within the blood vessel 60 and are designated as the first reflected light 132 and the second reflected light 152. First and second photodetectors 130, 150 of the device module 110 receive the first and second reflected lights 132, 152 after the first and second reflected lights 122, 142 pass back through the tissue 55 along with the first and second scattered lights 131, 151.

FIG. 2 is a graph illustrating a light absorption coefficient as a function of wavelength and oxygen level of the blood 62 where the light absorption coefficient defines a portion of the light that is absorbed (i.e., not reflected). As shown, the first and second reflected lights 132, 152 may be affected by the nature/status of the blood 62 with the blood vessel 60. The blood vessel 60 may be an artery carrying oxygenated blood or a vein carrying deoxygenated blood. More specifically, an arterial blood may generally include a higher concentration of Oxy hemoglobin vs Deoxy hemoglobin, where a venous blood may include a higher concentration of Deoxy hemoglobin vs Oxy hemoglobin. As shown in the graph of FIG. 2, an absorption coefficient 211 of the first light 122 is generally greater for Deoxy hemoglobin than the absorption coefficient 212 for Oxy hemoglobin. Accordingly, the absorption of the first light 122 is greater for venous blood than for arterial blood. As also shown in the graph of FIG. 2, the absorption coefficient 222 of the second light 142 is generally greater for Oxy hemoglobin than the absorption coefficient 221 for Deoxy hemoglobin. Accordingly the absorption of the second light 142 is greater for arterial blood than for venous blood.

Applying the light absorbing phenomena to the illustrated embodiment, the blood 62 is exposed to the first light 122. A first portion of the first light 122 is absorbed by the blood 62 and a second portion of the first light 122 defines the first reflected light 132. In the case where the blood vessel 60 is a vein, the relatively higher absorption coefficient 211 of the venous blood allows a relatively lower portion of the first light 122 to be included in the first reflected light 132. Conversely, in the case where the blood vessel 60 is an artery, the relatively lower absorption coefficient 212 of the arterial blood allows a relatively higher portion of the first light 122 to be included in the first reflected light 132. By way of summary, when the blood vessel 60 is a vein, the first reflected light 132 will have a lower intensity than when the blood 60 vessel is an artery.

In a similar fashion of applying the light absorbing phenomena to the illustrated embodiment, the blood 62 is exposed to the second light 142. A first portion of the second light 142 is absorbed by the blood 62 and a second portion of the second light 142 defines the second reflected light 152. In the case where the blood vessel 60 is a vein, the relatively lower absorption coefficient 221 of the venous blood allows a relatively higher portion of the second light 142 to be included in the second reflected light 152. Conversely, in the case where the blood vessel 60 is an artery, the relatively higher absorption coefficient 222 of the arterial blood allows a relatively lower portion of the second light 142 to be included in the second reflected light 152. By way of summary, when the blood vessel 60 is a vein, the second reflected light 152 will have a higher intensity than when the blood 60 vessel is an artery.

Figure 3:
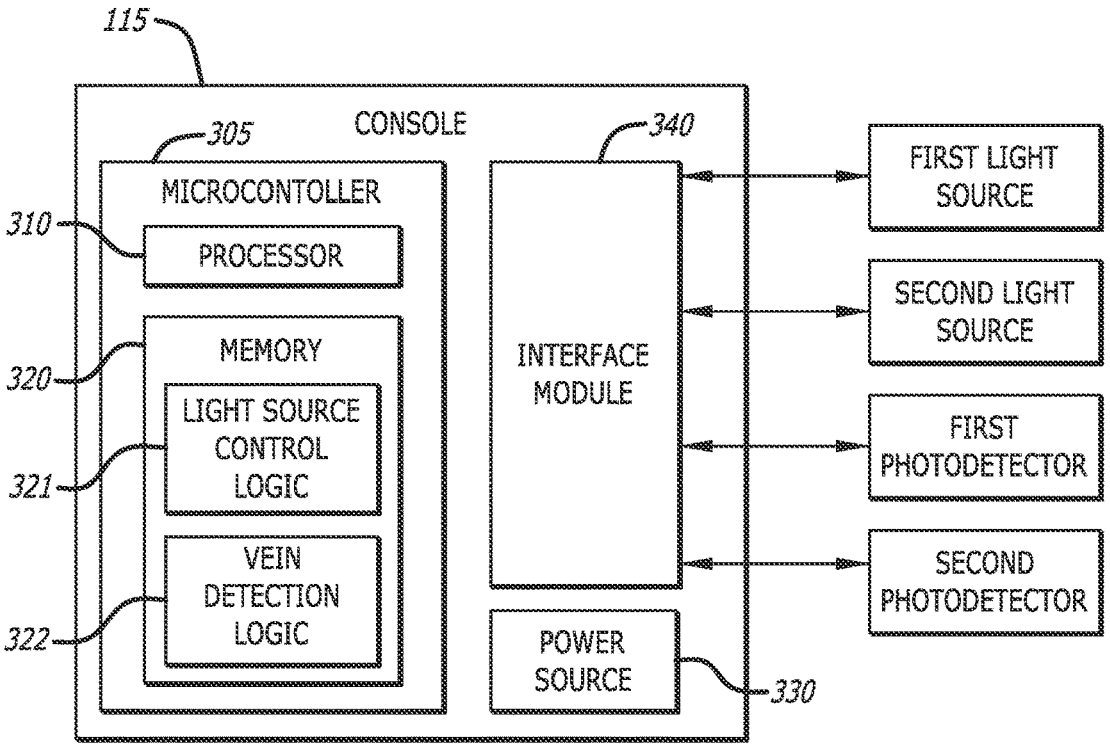
FIG. 3 illustrates a block diagram of a console of the device of FIG. 1A, in accordance with some embodiments.

FIG. 3 is a block diagram of the console 115 coupled with the first and second light sources 120, 140 and the first and second light photodetectors 130, 150. The console 115 is generally configured to govern the operation of the device module 110. The console 115 includes a processor 310 and memory 320 (e.g., a non-transitory computer-readable medium) having logic modules stored thereon, such as light source control logic 321 and vein detection logic 322. In the illustrated embodiment, the processor 310 and memory 320 may be incorporated into a microcontroller 305. The console 115 is powered via a power source 330, such as a battery that may be rechargeable.

The console 115 includes an interface module 340 coupled between the microcontroller 305 and the first and second light sources 120, 140 and the first and second light photodetectors 130, 150. The interface module 340 includes electrical components (e.g., transistors) that enable the microcontroller to control the operation of the first and second light sources 120, 140. The interface module 340 further includes electrical components (e.g., filters, amplifiers, analog to digital converters) configured to convert electrical signals from the first and second light photodetectors 130, 150 into digital data that can be processed by the vein detection logic 322.

The light source control logic 321 is configured to govern the operation of the first and second light sources 120, 140, i.e. energizing and de-energizing the first and second light sources 120, 140. In the illustrated embodiment, the light source control logic 321 may cause either or both of the first and second light sources 120, 140 to pulse at a rate of 30-40 pulses per second.

The vein detection logic 322 is generally configured to receive and process light data originating from the first and second light photodetectors 130, 150 and pertaining to the first and second scattered lights 131, 151 and the first and second reflected lights 132, 152. Operations of the vein detection logic 322 may include determining one or more parameters of the first and second reflected lights 132, 152.

Figure 4:
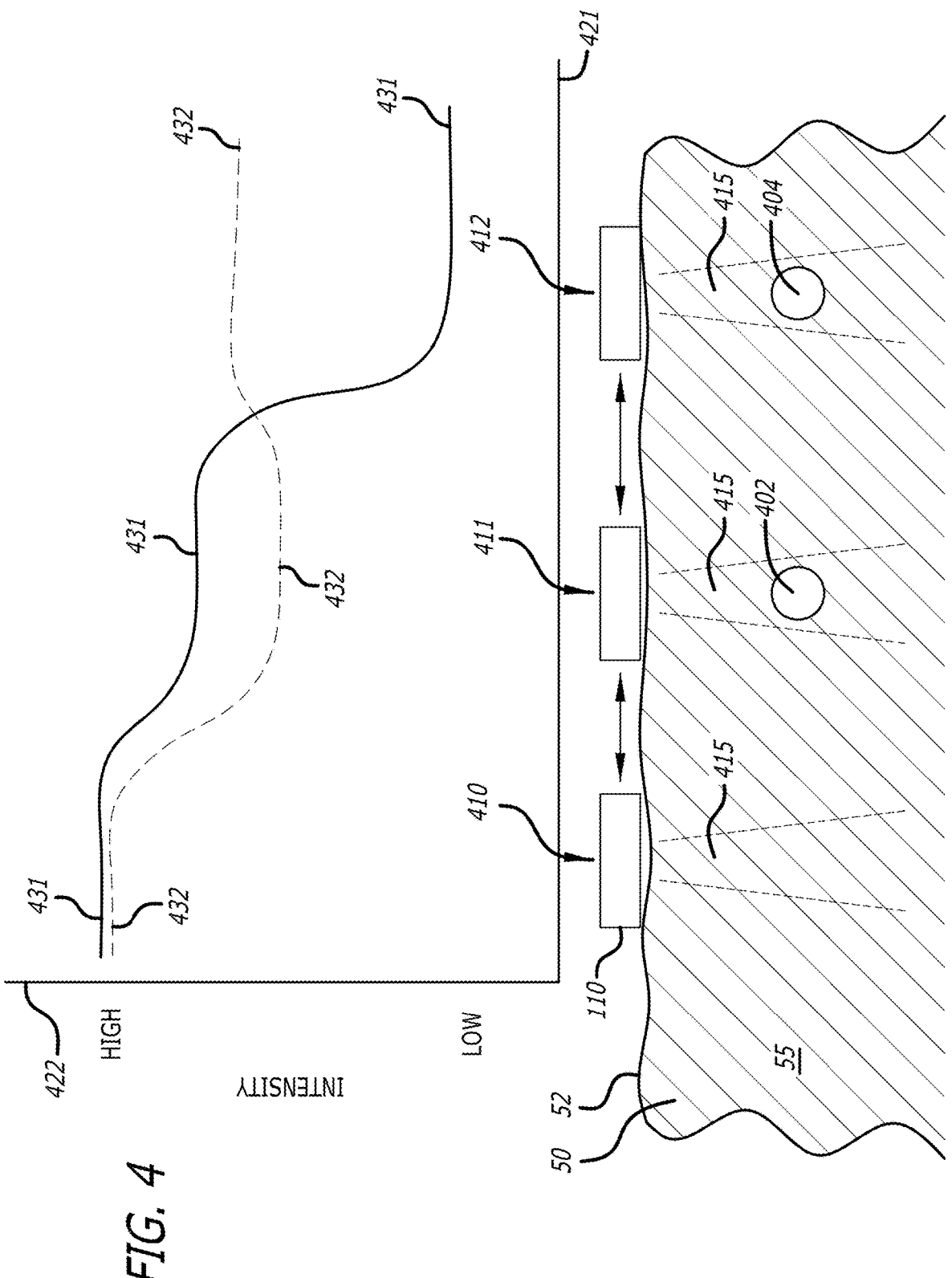
FIG. 4 illustrates an exemplary use case of the device of FIG. 1A, in accordance with some embodiments.

FIG. 4 illustrates an exemplary use case of the device 100 according to some embodiments. Shown is the device module 110 placed at three different locations 410, 411, and 412 along the skin surface 52 of the patient. At location 410, the device module 110 is located such that a detection area 415 beneath the device module 110 does not include a blood vessel. At location 411, the detection area 415 includes an artery 402 and at location 412, the detection area 415 includes a vein 404. FIG. 4 further illustrates an exemplary graph having a horizontal axis 421 extending along the skin surface 52 including the locations 410, 411, and 412 and a vertical axis 422 indicated an intensity level of reflected light. A first line 431 of the graph indicates an intensity of the light within the red spectrum received by the first photodetector 130 at the three locations 410, 411, and 412, and a second line 432 of the graph indicates an intensity of the light within the infrared spectrum received by the second photodetector 150 at the three locations 410, 411, and 412.

At location 410, where there is no blood vessel to absorb the light, the first line 431 indicates a "high" intensity detected by the first photodetector 130 and the second line 432 indicates a "high" intensity detected by the second photodetector 150. At the location 411, where there is the artery 402 present within the detection area 415, the intensity detected by the first photodetector 130 is reduced according to the absorption coefficient 212 (FIG. 2). Similarly, the intensity detected by the second photodetector 150 is reduced according to the absorption coefficient 222 (FIG. 2). At the location 412, where there is the vein 404 present within the detection area 415, the intensity detected by the first photodetector 130 is further significantly reduced with respect to the intensity at position 411 according to the absorption coefficient 211 (FIG. 2). Conversely, the intensity detected by the second photodetector 150 is increased with respect to the intensity at position 411 according to the absorption coefficient 221 (FIG. 2).

The vein detection logic 322 is configured to determine the presence of a blood vessel disposed beneath the device module 110. According to one embodiment, the vein detection logic 322 may determine (i) the first intensity of the reflected light received by the first photodetector 130 including the first scattered light 131 and the first reflected light 132 and a second intensity of the reflected light received by the second photodetector 150 including the second scattered light 151 and the second reflected light 152. The vein detection logic may utilize the first intensity, the second intensity or a combination of the first and second intensities to determine if a blood vessel is present beneath the device model 110. For example, as illustrated in FIG. 4, the first and second intensities at locations 411 and 412 are reduced with respect to the first and second intensities at the location 411. As such, the vein detection logic 322 may determine that either the artery 402 or the vein 404 are present with the detection area 415 based on a reduction of reflected light intensity, i.e., the reduction of the first intensity, the reduction of the second intensity, or a reduction of combination of the first and second intensities.

In an exemplary instance of use, the clinician may displace the device module 110 across the skin surface 52 in search of a vein. When the device module 110 is positioned over a blood vessel, the vein detection logic 322 may detect a decrease in the intensity of reflected light as described above. According to one embodiment, the vein detection logic 322 may compare an instant reflected light intensity with an intensity limit stored in the memory 320, and provide a notification when the instant reflected light intensity drops below the intensity limit stored in the memory 320. According to another embodiment, the vein detection logic 322 may monitor a trend of the instant reflected light intensity as the device module 110 is moved across the skin surface 52, i.e., across the location 410, 411, and 412 and provide a notification when a minimum instant reflected light intensity is detected.

The vein detection logic 322 is configured to determine that a blood vessel disposed beneath the device module 110 is a vein as opposed to an artery. According to one embodiment, the vein detection logic 322 may determine (i) a first intensity of the first scattered light 131 in combination with the first reflected light 132, i.e. light received by the first photodetector 130 that includes wavelengths within the red spectrum, e.g., a wavelength of 660 nm), and (ii) a second intensity of the second scattered light 151 in combination with the second reflected light 152, i.e. light received by the second photodetector 150 that includes a wavelengths within the infrared spectrum, e.g., a wavelength of 940 nm. The vein detection logic 322 may then compare the first intensity with the second intensity, and if the second intensity is greater than the first intensity, the vein detection logic 322 may determine that the blood vessel is a vein. Conversely, if the first intensity is greater than the second intensity, the vein detection logic 322 may determine that the blood vessel is an artery. In other words, the vein detection logic 322 may determine that the blood vessel disposed is a vein or is an artery based on the difference between the first intensity and the second intensity.

According to another embodiment, the vein detection logic 322 may calculate a ratio of the first and second intensities (e.g., the first intensity divided by the second intensity). The vein detection logic 322 may then compare the calculated ratio with a ratio limit stored in the memory 320, as a result of the comparison determine that the blood is a vein or is an artery. For example, when the calculated ratio is less than the ratio limit, the vein detection logic 322 may determine that the blood vessel is a vein, and when the calculated ratio is greater than the ratio limit, the vein detection logic 322 may determine that the blood vessel is an artery. Calculating the ratio and making the determination based the ratio may provide for an increased reliability of the result over comparing the intensities directly by reducing the effects of variation associated with the first and second scattered lights 131, 151.

FIG. 5 is a block diagram of a method 500 of detecting a blood vessel with in a patent that, according to some embodiments, includes all or any subset of the following actions, steps, or operations. Each block illustrated in FIG. 5 represents an operation of the method 500 performed by a blood vessel or vein detection device, and typically as a result of execution of one or more logic modules disclosed herein as well as deployment of specific devices, such as the blood vessel detection device 100. The method 500 may include projecting a first and second lights having different wavelengths through tissue of a detection area of the patient (block 510). In some embodiments of the method 500, the first wavelength is within the red spectrum (e.g., 660 nm), and the second wavelength is within the infrared spectrum (e.g., 940 nm). The method 500 may further include receiving first and second reflected lights resulting from the first and second lights where the first and second reflected lights define first and second intensities, respectively (block 520).

The method 500 may further include calculating a first parameter based on the first and second intensities and comparing the parameter with a defined parameter limit (block 530). In some embodiments of the method 500, the first parameter is a combination of the first and second intensities. The method 500 may further include determining, as a result of the comparison, that a blood vessel is present within the detection area when the parameter exceeds the defined limit (block 540). The method 500 may further include providing a visual or audible notification that a blood vessel is present within the detection area when the parameter exceeds the defined limit (block 550). The method 500 may further include calculating a difference between the first and second intensities and determining from the difference that the blood vessel is a vein vs an artery (block 560). In some embodiments of the method 500, determining from the difference may include comparing the difference with a defined difference limit and determining, as a result of the comparison, that the blood vessel is a vein. The method 500 may further include providing a visual or audible notification that a vein is present within the detection area when the difference exceeds a defined difference limit.

The method 500 may further include calculating a ratio of the first and second intensities and determining from the ratio that the blood vessel is a vein vs an artery (block 570). In some embodiments, the method 500 may include comparing the ratio with a defined ratio limit and determining, as a result of the comparison, that the blood vessel is a vein The method 500 may further include providing a visual or audible notification that a vein is present within the detection area when the ratio exceeds the defined ratio limit.

In some embodiments of the method 500, calculating the ratio includes dividing the first intensity by the second intensity, and exceeding the defined ratio limit is defined by the ratio having a greater numerical value than the defined ratio limit.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A blood vessel detection device, comprising:
   a device module configured for placement on a skin surface of a patient, the device module including:
      a first light source configured to project a first light having a first wavelength through the skin surface and into a detection area of the patient, the detection area located beneath the device module;
      a second light source configured to project a second light having a second wavelength through the skin surface and into the detection area, the second wavelength different from the first wavelength;
      a photodetector configured to receive a first reflected light resulting from the first light and a second reflected light resulting from the second light, wherein the first light source, the second light source and the photodetector are arranged in a linear array; and
   a console coupled with the first light source, the second light source, and the photodetector, the console having a microcontroller that includes a processor and a memory having logic stored thereon that, when executed by the processor, performs operations that include:
      activating the first light source and the second light source to the first light and the second light into the detection area, wherein the console includes an interface module coupled between the first light source and the second light source, the interface module having electrical components that enable control of the first light source and the second light source by the processor;
      receiving first light data originating from the photodetector including a first intensity of the first reflected light;

receiving second light data originating from the photodetector including a second intensity of the second reflected light;

calculating a first parameter of the first intensity and the second intensity;

determining from the first parameter that a blood vessel is present within the detection area;

calculating a second parameter of the first intensity and the second intensity; and determining from the second parameter that the blood vessel present within the detection area is a vein or is an artery;

wherein the second parameter is a ratio of the first intensity and the second intensity, the ratio defined by the first intensity divided by the second intensity; and wherein determining from the second parameter that the blood vessel present within the detection area is a vein or is an artery includes:

comparing the ratio with a ratio limit stored in the memory and, as a result of the comparing, determining that the blood vessel is a vein when the ratio is less than the ratio limit; and wherein the operations further include:

providing a notification that the blood vessel is present within the detection area.

2. The blood vessel detection device according to claim 1, wherein:

the first wavelength is within a red spectrum, and the second wavelength is within an infrared spectrum.

3. The blood vessel detection device according to claim 2, wherein:

the first wavelength is 660 nm, and the second wavelength is 940 nm.

4. The blood vessel detection device according to claim 1, wherein the first parameter is a combination of the first intensity and the second intensity.

5. The blood vessel detection device according to claim 1, wherein determining a presence of the blood vessel includes:

comparing a combination of the first intensity and the second intensity with an intensity limit stored in the memory; and determining that the blood vessel is present within the detection area when the combination of the first intensity and the second intensity is less than the intensity limit.

6. The blood vessel detection device according to claim 1, wherein the operations include pulsing the first light source and the second light source at a rate between 30 and 40 pulses per second.

7. The blood vessel detection device according to claim 1, further comprising an attachment mechanism coupled with the device module, the attachment mechanism configured to secure the device module to the patient.

8. The blood vessel detection device according to claim 7, wherein the attachment mechanism includes a band or strap configured to extend around an extremity of the patient.

9. The blood vessel detection device according to claim 1, wherein:

the device module further includes a number of visual notification devices or a number of audio notification devices, and the operations further include providing the notification using at least one of the number of visual notification devices or the number of audio notification devices when the blood vessel is present within the detection area.

10. The blood vessel detection device according to claim 1, wherein:

the device module further includes a number of visual notification devices or a number of audio notification devices, and the operations further include providing the notification using at least one of the number of visual notification devices or the number of audio notification devices when the blood vessel present within the detection area is determined to be a vein.

* * * * *